(12) United States Patent
Yamanaka et al.

(10) Patent No.: US 7,550,553 B2
(45) Date of Patent: Jun. 23, 2009

(54) FLUORINATED DIAMINE AND POLYMER MADE FROM THE SAME

(75) Inventors: Kazuhiro Yamanaka, Tokyo (JP); Kazuhiko Maeda, Tokyo (JP)

(73) Assignee: Central Glass Company, Limited, Ube-Shi (JP)

( * ) Notice: Subject to any disclaimer, the term of this patent is extended or adjusted under 35 U.S.C. 154(b) by 278 days.

(21) Appl. No.: 11/667,823

(22) PCT Filed: Dec. 26, 2005

(86) PCT No.: PCT/JP2005/023757

§ 371 (c)(1),
(2), (4) Date: May 16, 2007

(87) PCT Pub. No.: WO2006/070728

PCT Pub. Date: Jul. 6, 2006

(65) Prior Publication Data

US 2008/0221298 A1    Sep. 11, 2008

(30) Foreign Application Priority Data

Dec. 28, 2004 (JP) ............................. 2004-381143

(51) Int. Cl.
*C08G 69/26* (2006.01)
(52) U.S. Cl. ..................... 528/347; 528/335; 528/350; 528/353; 528/289; 528/291; 528/342; 528/348; 560/19
(58) Field of Classification Search ............. 560/19
See application file for complete search history.

(56) References Cited

U.S. PATENT DOCUMENTS 5,055,116 A    10/1991    Kohn et al.

(Continued)

FOREIGN PATENT DOCUMENTS

JP    2001-100055 A    4/2001
JP    2003-183387 A    7/2003

(Continued)

OTHER PUBLICATIONS

European Search Report dated Dec. 12, 2008 (Six (6) pages).
"The Latest Polyimide—Basic and Application—"; edited by Japan Polyimide Study Group; pp. 269-283; 2002.
"Nitto Giho"; vol. 28, No. 2, Oct. 1990, pp. 49-56.
International Search Report dated Feb. 21, 2006 with English translation of relevant portion (Three (3) pages).

*Primary Examiner*—Randy Gulakowski
*Assistant Examiner*—Rachel Kahn
(74) *Attorney, Agent, or Firm*—Crowell & Moring LLP

(57) ABSTRACT

A fluorine-containing diamine represented by the formula (1), [Chemical Formula 29]

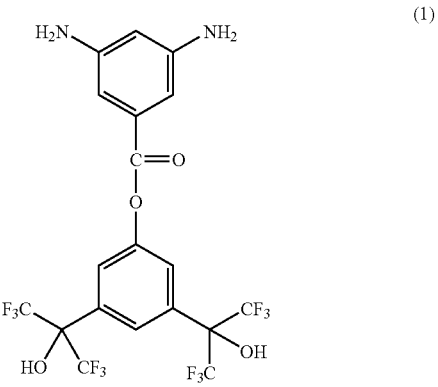

is provided. Furthermore, a fluorine-containing polymer is provided by using this fluorine-containing amine as a monomer. The fluorine-containing polymer can exhibit superior characteristics such as low dielectric property and high transparency, while maintaining high fluorine content and retaining adhesive property.

6 Claims, 4 Drawing Sheets

U.S. PATENT DOCUMENTS 6,810,189 B2  10/2004  Ido et al.
7,112,647 B2   9/2006  Taguchi et al.
7,125,943 B2  10/2006  Sumida et al.

FOREIGN PATENT DOCUMENTS

FLUORINATED DIAMINE AND POLYMER MADE FROM THE SAME

TECHNICAL FIELD

The present invention relates to a novel hexafluoroisopropanol group-containing diamine or its derivative and to a polymer obtained by using the hexafluoroisopropanol group-containing diamine or its derivative.

BACKGROUND OF THE INVENTION

In general, diamine is used as a monomer for a condensation or addition polymerization of polyimide, polyamide, polyurea, etc. Since the obtained polymers have ring structures as main structure in the molecules, they have many characteristics in which they are large in mechanical strengths such as tensile strength and bending strength and in which they are superior in thermal stability such as thermal decomposition temperature and thermal deformation temperature. Thus, they are regarded as high-performance engineering plastics.

Regarding these resins, there have been made various applications such as engineering plastics, heat-resistant coating materials, electronic materials, electronic component materials, and optical materials. In particular, when the uses to semiconductors and optical members are assumed, low dielectric constant property and high transparency are required as a result of an increasing need for high-speed processing use and high-frequency use together with the development of communication equipment. Being low in thermal expansion is also said to be an important point. As a means for providing such low dielectric constant and a means for providing such high transparency, fluorine-containing polymers, which lower electron density, are actively studied. For example, Non-patent Publication 1 has a description of lowering a fluorine-containing polyimide in dielectric constant, and Non-patent publication 2, which is cited therein, discloses that dielectric constant becomes low by increasing the fluorine content.

Since fluorine-containing compounds are used in a wide applied field by centering on the leading-edge filed, since they have characteristics, such as low water absorption, heat resistance, weather resistance, corrosion resistance, transparency, low refractive index property and low dielectric property, resulting from possessing fluorine atom. They are applied mainly in the coating field at each wavelength.

Hitherto, there have been known methods of introducing a long-chain perfluoroalkyl and of replacing hydrogen of aromatic ring with fluorine, as a method of increasing the fluorine content in the fluorine-containing polymer. In many cases, however, these methods lower adhesion property of the polymer to silicon substrate. For example, although Patent Publication 3 discloses an invention of an optical waveguide constituted by a fluorine-containing polyimide, it discloses that there is a need of forming an adhesion layer for improving adhesion with substrate. Thus, there has been a demand for a fluorine-containing polymer exhibiting characteristics such as low dielectric property and high transparency, while maintaining high fluorine content and retaining adhesion property.

Non-patent Publication 1: "The Latest Polyimide-Basic and Application-" edited by Japan Polyimide Study Group, P 269-283 (2002)

Non-patent Publication 2: "Nitto Giho", 28(2), 49, (1990)

Patent Publication 1: Japanese Patent Laid-open Publication No. 2001-100055

SUMMARY OF THE INVENTION

The present invention was made in view of the above-mentioned problems. Its task is to provide a fluorine-containing polymer exhibiting characteristics, such as low dielectric property and high transparency, for having low dielectric property and high transparency and for accomplishing high solubility in an alkali aqueous solution used as the developing solution and in the organic solvent, high adhesion property to substrate, and high film-forming property, while maintaining high fluorine content and retaining adhesion property.

The present inventors have eagerly examined the development of a novel diamine to solve the above-mentioned task. With this, we have found a monomer that hexafluoroisopropanol groups are introduced into the same molecule. Various examinations on its polymers have led to the accomplishments of dielectric constant lowering, transparency improvement, high solubility in an alkali aqueous solution used as the developing solution and in the organic solvent, high adhesion property to substrate and high film-forming property, thereby completing the present invention. A hexafluoroisopropanol group-containing polymer used in the present invention can exhibit characteristics, such as low dielectric property and high transparency, while maintaining adhesion property, since it contains fluorine and hydroxy group.

It is an object of the present invention to provide a novel, hexafluoroisopropanol group-containing diamine that becomes a starting material of fluorine-containing polymers having the above-mentioned superior characteristics.

It is another object of the present invention to provide polymers and acid-labile compounds by using derivatives of the diamine and a hexafluoroisopropanol group-containing diamine or its derivatives.

According to the present invention, there is provided a fluorine-containing diamine represented by the formula (1).

[Chemical Formula 1]

Furthermore, according to the present invention, there are provided three kinds of fluorine-containing polymers derived from the fluorine-containing diamine (monomer). The first polymer is a fluorine-containing polyamide acid. This polyamide acid is a polymer obtained by reacting the diamine, which is represented by the formula (1), with a tetracarboxylic acid represented by the formula (2),

(2)

or tetracarboxylic dianhydride represented by the formula (3), (3)

and is a polymer represented by the formula (4), (4)

(In the formulas (2), (3) and (4), R is a tetravalent organic group containing an aromatic ring, and the carbonyl carbons are bonded to the aromatic ring in the ortho positions each other to form imide five-membered rings).

The second polymer is a fluorine-containing polyimide resin (hereinafter may be abbreviated as "fluorine-containing polyimide"). This fluorine-containing polyimide resin is a polymer obtained by dehydrating the fluorine-containing polyamide acid and is a polymer represented by the formula (5), (5)

(In the formula, R is the same as in the formula (4)).

The third polymer is a fluorine-containing polyamide resin (hereinafter may be abbreviated as "fluorine-containing polyamide"). This fluorine-containing polyamide resin is a polymer obtained by reacting the diamine, which is represented by the formula (1), with one selected from a dicarboxylic acid, a dicarboxylic halide and a dicarboxylic diester, which are represented by the formula (6), (6)

(In the formula, $R^1$ is a bivalent organic group containing an aromatic ring. X is —OH group, halogen (fluorine, chlorine, bromine or iodine) atom or —OR' group, and R' represents an alkyl group or phenyl group.), and is a polymer containing a constituent unit represented by the formula (7), (7)

(In the formula, $R^1$ is the same as in the formula (6)).

DETAILED DESCRIPTION

The present invention provides a novel fluorine-containing polyimide or its precursor, a fluorine-containing polyamide acid, and their polymers, which exhibit characteristics such as low dielectric property and high transparency, while maintaining high fluorine content and retaining adhesion property.

Fluorine-containing polymers of the present invention are low in dielectric constant and thermal expansion coefficient and show a good solubility in the organic solvent and an alkali aqueous solution that is the developing solution, while maintaining characteristics such as mechanical strength and thermal stability. Therefore, they are useful as insulating materials of electrical and electronic parts and as coating members of optical parts.

In the following, the present invention is described in detail.

The present invention relates to a hexafluoroisopropanol group-containing diamine represented by the formula (1) (hereinafter referred to as the fluorine-containing diamine (1)) and its application. Furthermore, it relates to polymers or acid-labile compounds obtained by using the fluorine-containing diamine (1) as a starting raw material. The process for producing the fluorine-containing diamine (1) of the present invention is not particularly limited. It can be easily produced by using 3,5-dinitrobenzoyl chloride and a compound represented by the formula (8),

[Chemical Formula 8]

(8)

as raw materials and by their condensation reaction and a reduction of nitro groups.

For example, in a condensation reaction between 3,5-dinitrobenzoyl chloride and the compound represented by the formula (8), there is taken a process where the reaction is conducted by dissolving both raw materials in an organic solvent, or a process where the reaction is conducted with no solvent by dissolving (melting) both raw materials with each other. There is cited a process where the reaction is conducted preferably in the presence of both raw materials of equimolecular quantities within temperature ranges of −20 to 80° C. in an organic solvent and of 100 to 250° C. in the case of using no solvent. If it is lower than these temperature ranges, the reaction does not proceed. If it is higher than those, side reactions tend to occur. Furthermore, in this condensation reaction, it can be used 3,5-dinitrobenzoic acid in place of 3,5-dinitrobenzoyl chloride.

In the reduction reaction of the nitro groups of the nitro compound obtained by the condensation reaction, there is taken a catalytic hydrogenation method using hydrogen gas or a chemical hydrogenation method normally using metal and acid. Preferably, there is cited a method in which the reaction is conducted by bringing the nitro compound into contact with hydrogen gas in the presence of a palladium or platinum catalyst, in an organic solvent, in a temperature range of 20-100° C.

The organic solvent used in these condensation reaction and reduction reaction is not particularly limited, as long as the raw materials or the reaction products are dissolved therein. Without a particular limitation, it can be used N,N-dimethylformamide (DMF), N,N-dimethylacetamide (DMAc), dimethylsulfoxide (DMSO), phenol, o-cresol, N-methyl-2-pyrolidone, sulfolane, m-cresol, p-cresol, 3-chlorophenol, 4-chlorophenol, γ-butyrolactone, γ-valerolactone, δ-valerolactone, γ-caprolactone, ε-caprolactone, α-methyl-γ-butyrolactone, ethylene carbonate, propylene carbonate, triethylene glycol, acetophenone, 1,3-dimethyl-2-imidazolidinone, butyl acetate, ethyl acetate, ethylcellosolve, butylcellosolve, 2-methylcellosolve acetate, ethylcellosolve acetate, butylcellosolve acetate, ethyl acetate, butyl acetate, isobutyl acetate, dibutyl ether, diethylene glycol dimethyl ether, propylene glycol methyl acetate, tetrahydrofuran, dimethoxyethane, diethoxyethane, methyl isobutyl ketone, diisobutyl ketone, cyclohexanone, methyl ethyl ketone, acetone, butanol, ethanol, methanol, xylene, toluene, chlorobenzene, terpene, mineral spirit, petroleum naphtha-series solvents, and the like.

Polymers according to the present invention are produced by using the fluorine-containing diamine represented by the formula (1) or its derivatives. Although the polymers are not particularly limited, there are cited polyimide, polyamide, polyamine, polyurea, polyamide acid that is their precursor and the like, and copolymers obtained by combining condensation reactions of several kinds of these, such as polyamide-imide and polyester-imide. In particular, polyimide is expected to have various applications as an electronic material or optical material, which is provided with high heat resistance.

The production process of the fluorine-containing polymers of the present invention is not particularly limited. The polymerizations are conducted by using amides, esters and ether-forming derivatives, which have been synthesized from the fluorine-containing diamine (1), as monomers, by mechanisms, such as condensation, addition polymerization and polyaddition, with pairing monomers that are capable of reacting with their reactive functional groups. Therefore, diol compounds are used as the pairing monomers in the case of synthesizing polyesters and polyethers, and diamine compounds are used as the pairing monomers in the case of synthesizing polyamides. The structures of these pairing monomers usable in the present invention are not particularly limited, and known compounds can be used.

In case that the fluorine-containing diamine (1) or its amide-forming derivative has been used in the production of the fluorine-containing polyimide and the fluorine-containing polyamide of the present invention, it can be copolymerized another amine component or its amide-forming derivative. The diamine compounds usable together are not particularly limited. Specifically, they can be exemplified by 3,5-diaminobenzotrifluoride, 2,5-diaminobenzotrifluoride, 3,3'-bistrifluoromethyl-4,4'-diaminobiphenyl, 3,3'-bistrifluoromethyl-5,5'-diaminobiphenyl, bis(trifluoromethyl)-4,4'-diaminodiphenyl, bis(fluorinated alkyl)-4,4'-diaminodiphenyl, dichloro-4,4'-diaminodiphenyl, dibromo-4,4'-diaminodiphenyl, bis(fluorinated alkoxy)-4,4'-diaminodiphenyl, diphenyl-4,4'-diaminodiphenyl, 4,4'-bis(4-aminotetrafluorophenoxy)tetrafluorobenzene, 4,4'-bis(4-aminotetrafluorophenoxy)octafluorobiphenyl, 4,4'-binaphthylamine, o-, m- and p-phenylenediamine, 2,4-diaminotoluene, 2,5-diaminotoluene, 2,4-diaminoxylene, 2,4-diaminodiurene, dimethyl-4,4'-diaminodiphenyl, dialkyl-4,4'-diaminodiphenyl, dimethoxy-4,4'-diaminodiphenyl, diethoxy-4,4'-diaminodiphenyl, 4,4'-diaminodiphenylmethane, 4,4'-diaminodiphenyl ether, 3,4'-diaminodiphenyl ether, 4,4'-diaminodiphenyl sulfone, 3,3'-diaminodiphenyl sulfone, 4,4'-diaminobenzophenone, 3,3'-diaminobenzophenone, 1,3-bis(3-aminophenoxy)benzene, 1,3-bis(4-aminophenoxy)benzene, 1,4-bis(4-aminophenoxy)benzene, 4,4'-bis(4-aminophenoxy)biphenyl, bis(4-(3-aminophenoxy)phenyl)sulfone, bis(4-(4-aminophenoxy)phenyl)sulfone, 2,2-bis(4-(4-aminophenoxy)phenyl)propane, 2,2-bis(4-(4-aminophenoxy)phenyl)hexafluoropropane, 2,2-bis(4-(3-aminophenoxy)phenyl)propane, 2,2-bis(4-(3-aminophenoxy)phenyl)hexafluoropropane, 2,2-bis(4-(4-amino-2-trifluoromethylphenoxy)phenyl)hexafluoropropane, 2,2-bis(4-(3-amino-5-trifluoromethylphenoxy)phenyl)hexafluoropropane, 2,2-bis(4-aminophenyl)hexafluoropropane, 2,2-bis(3-aminophenyl)hexafluoropropane, 2,2-bis(3-amino-4-hydroxyphenyl)hexafluoropropane, 2,2-bis(3-amino-4-methylphenyl)hexafluoropropane, 4,4'-bis(4-aminophenoxy)octafluorobiphenyl, 4,4'-diaminobenzanilide, and the like. It is possible to use two kinds or more of these diamine compounds together.

The fluorine-containing polyamide acid of the present invention is a fluorine-containing polyamide acid represented by the formula (4) (In the formula, R is a tetravalent organic group containing an aromatic ring, and the carbonyl carbons are bonded to the aromatic ring in the ortho positions each other to form imide five-membered rings.).

The fluorine-containing polyimide in the present invention is a fluorine-containing polyimide containing a constituent unit represented by the formula (5) (In the formula, R is a tetravalent organic group containing an aromatic ring, and the carbonyl carbons are bonded to the aromatic ring in the ortho positions each other to form imide five-membered rings.).

The fluorine-containing polyimide of the present invention is a polymer that is formed of a constituent unit represented by the formula (5) or a polymer that the constituent unit is in a range of 1-100 mol %. In case that the constituent unit represented by the formula (5) is less than 1 mol %, dielectric constant of the film obtained therefrom does not become sufficiently low. Therefore, it is not preferable.

R in the formula (4) or (5) is not particularly limited in structure, as long as it is a tetravalent organic group containing an aromatic ring. It can be exemplified by a group represented by the following formula,

[Chemical Formula 9]

or the following formula.

[Chemical Formula 10]

Herein, in the formula, each of Y is independently a single bond, —O—, —S—, —SO$_2$—, —CO—, —CH$_2$—, —C(CH$_3$)$_2$—, —CF$_2$—, or —C(CF$_3$)$_2$—, and each of m and n is an integer of 0-3. The benzene rings in these formulas may suitably be replaced with C$_1$-C$_5$ lower alkyl groups and halogen atoms such as chlorine, bromine and fluorine. Herein, one in which m is 0 and n is 1 is particularly preferable. For example, the substituent of the formula (3) can be shown as an example. The benzene rings in these formulas may suitably be replaced with C$_1$-C$_5$ lower alkyl groups and halogen atoms such as chlorine, bromine and fluorine.

The tetracarboxylic dianhydride usable in the present invention is not particularly limited in structure. For example, there are cited trifluoromethylbenzenetetracarboxylic dianhydride, bistrifluoromethylbenzenetetracarboxylic dianhydride, difluorobenzenetetracarboxylic dianhydride, biphenyltetracarboxylic dianhydride, terphenyltetracarboxylic dianhydride, hexafluoroisopropylidenediphthalic dianhydride, oxydiphthalic dianhydride, bicyclo(2,2,2)oct-7-ene-2,3,5,6-tetracarboxylic dianhydride, 2,2-bis(3,4-dicarboxyphenyl)hexafluoropropanoic dianhydride (6FDA), and the like.

The fluorine-containing polyimide and its precursor, the fluorine-containing polyamide acid, of the present invention can be produced by reacting the diamine component with the tetracarboxylic acid dianhydride. This polymerization reaction is not particularly limited in method and condition. It is possible to obtain an almost or perfectly ring-closed polyimide, for example, by a process in which the diamine component and the tetracarboxylic acid dianhydride are reacted by dissolving (melting) them each other in a temperature range of 100-250° C., preferably 150-200° C., with no solvent, or by a process in which they are reacted in an organic solvent at high temperature (a temperature range of 100-250° C., preferably 150-200° C.). Furthermore, there are taken a process of obtaining a fluorine-containing polyamide acid represented by the formula (4) as the precursor, which is not ring-closed or only partly ring-closed, by reacting the diamine component and the tetracarboxylic acid dianhydride at a temperature of −20 to 80° C. in an organic solvent, and like processes.

It is possible to make a fluorine-containing polyamide acid or partly ring-closed imide that is the precursor, into a polyimide, through ring closure in a temperature range of 100-350° C., preferably 250-300° C., by suitably adding, according to need, a ring-closing agent, such as acid anhydrides, for example, acetic anhydride, propionic anhydride and benzoic anhydride, and dicyclohexylcarbodiimide, and a ring-closing catalyst, such as pyridine, isoquinoline, trimethylamine, aminopyridine and imidazole.

Upon conducting these polymerization reactions, a diester dicarboxylic acid derivative obtained by subjecting the tetracarboxylic dianhydride to ring opening with an alcohol, and its dihalide derivative can be polymerized with the diamine. In particular, the polyimide precursor in this case is a polyamide acid ester, and it is superior to polyamide acid in terms of long-term storage stability and the like.

The fluorine-containing polyamide of the present invention is a polymer compound containing a constituent unit represented by the formula (7) (In the formula, $R^1$ is a bivalent organic group containing an aromatic ring.).

$R^1$ in the formula (7) is not particularly limited in its structure, as long as it is a bivalent organic group containing an aromatic ring. A group represented by the following formula,

[Chemical Formula 11]

or the following formula,

[Chemical Formula 12]

can be shown as an example.

Herein, in the formula, each of Y is independently a single bond, —O—, —S—, —SO$_2$—, —CO—, —CH$_2$—, —C(CH$_3$)$_2$—, —CF$_2$—, or —C(CF$_3$)$_2$—, and m is an integer of 0-3. The benzene rings in these formulas may suitably be replaced with $C_1$-$C_5$ lower alkyl groups and halogen atoms such as chlorine, bromine and fluorine. The benzene rings in these formulas may suitably be replaced with $C_1$-$C_5$ lower alkyl groups and halogen atoms such as chlorine, bromine and fluorine.

Dicarboxylic acid, dicarboxylic dihalide and dicarboxylic diester, which are usable in the present invention and represented by the formula (6), are not particularly limited in their structures. Generally known, corresponding compounds can be widely used. Fluorine, chlorine, bromine and iodine atoms are cited as halogen atoms used in the dicarboxylic dihalide. In particular, dicarboxylic dichloride and dicarboxylic dibromide using chlorine and bromine atoms are preferably used. R' of —OR$^{40}$ group used in the dicarboxylic diester is not particularly limited. There are cited $C_1$-$C_{10}$ alkyl groups, such as alkyl group, ethyl group, propyl group, butyl group, hexyl group and nonyl group; a phenyl group having an alkyl group substituted, such as methyl group or ethyl group, or unsubstituted phenyl group, and the like. In particular, dicarboxylic dimethyl ester, dicarboxylic diethyl ester, and dicarboxylic diphenyl ester using methyl group, ethyl group and phenyl group are preferably used.

More specifically, it is possible to exemplarily show aliphatic dicarboxylic acids, such as oxalic acid, malonic acid, succinic acid, glutaric acid, adipic acid, pimelic acid, suberic acid, azelaic acid and sebacic acid; and aromatic dicarboxylic acids such as phthalic acid, isophthalic acid, terephthalic acid, 3,3'-dicarboxyldiphenyl ether, 3,4'dicarboxyldiphenyl ether, 4,4'-dicarboxyldiphenyl ether, 3,3'-dicarboxyldiphenylmethane, 3,4'-dicarboxyldiphenylmethane, 4,4'-dicarboxyldiphenylmethane, 3,3'-dicarboxyldiphenyldifluoromethane, 3,4'-dicarboxyldiphenyldifluoromethane, 4,4'-dicarboxyldiphenyldifluoromethane, 3,3'-dicarboxyldiphenylsulfone, 3,4'-dicarboxyldiphenylsulfone, 4,4'-dicarboxyldiphenylsulfone, 3,3'-dicarboxyldiphenylsulfide, 3,4'-dicarboxyldiphenylsulfide, 4,4'-dicarboxyldiphenylsulfide, 3,3'-dicarboxyldiphenyl ketone, 3,4'-dicarboxyldiphenyl ketone, 4,4'-dicarboxyldiphenyl ketone, 2,2-bis(3-carboxyphenyl)propane, 2,2-bis(3,4'-dicarboxyphenyl)propane, 2,2-bis(4-carboxyphenyl)propane, 2,2-bis(3-carboxyphenyl) hexafluoropropane, 2,2-bis(3,4'-dicarboxyphenyl) hexafluoropropane, 2,2-bis(4-carboxyphenyl) hexafluoropropane, 1,3-bis(3-carboxyphenoxy)benzene, 1,4-bis(3-carboxyphenoxy)benzene, 1,4-bis(4-carboxyphenoxy)benzene, 3,3'-(1,4-phenylenebis(1-methylethylidene))bisbenzoic acid, 3,4'-(1,4-phenylenebis(1-methylethylidene))bisbenzoic acid, 4,4'-(1,4-phenylenebis(1-methylethylidene))bisbenzoic acid, 2,2-bis(4(3-carboxyphenoxy)phenyl)propane, 2,2-bis(4-(4-carboxyphenoxy)phenyl)propane, 2,2-bis(4-(3-carboxyphenoxy)phenyl)hexafluoropropane, 2,2-bis(4-(4-carboxyphenoxy)phenyl)hexafluoropropane, bis(4-(3-carboxyphenoxy)phenyl)sulfide, bis(4-(4-carboxyphenoxy)phenyl)sulfide, bis(4-(3-carboxyphenoxy)phenyl)sulfone, and bis(4-(4-carboxyphenoxy)phenyl)sulfone; and perfluorononenyloxy group-containing dicarboxylic acids such as 5-(perfluorononenyloxy)isophthalic acid, 4-(perfluorononenyloxy)phthalic acid, 2-(perfluorononenyloxy)terephthalic acid, and 4-methoxy-5-(perfluorononenyloxy)isophthalic acid; perfluorohexenyloxy group-containing dicarboxylic acids such as 5-(perfluorohexenyloxy)isophthalic acid, 4-(perfluorohexenyloxy)phthalic acid, 2-(perfluorohexenyloxy)terephthalic acid, and 4-methoxy-5-(perfluorohexenyloxy)isophthalic acid; and dicarboxylic dihalides and dicarboxylic diesters, which correspond to each of these carboxylic acids. In other words, there are cited dicarboxylic dihalides such as dichloride and dibromide of corresponding dicarboxylic acids; dicarboxylic dialkylesters such as dimethylester and diethylester thereof; dicarboxylic diphenylester; and the like. These may be alone or in a mixture of at least two.

It is possible to produce the fluorine-containing polyamide of the present invention by reacting the fluorine-containing diamine component represented by the formula (1) with the dicarboxylic acid, dicarboxylic dihalide or dicarboxylic diester, which is represented by the formula (6). This polymerization reaction is not particularly limited in method and condition. For example, there are cited a process in which the diamine component and an amide-forming derivative of the dicarboxylic acid are reacted by dissolving (melting) them each other in a temperature range of 100-250° C., preferably 150-200° C., with no solvent; a process in which they are reacted in an organic solvent at high temperature (a temperature range of 100-250° C., preferably 150-200° C.); and a process in which they are reacted at a temperature of −20 to 80° C. in an organic solvent.

Organic solvents usable for the polymerization reaction of the fluorine-containing polymer (the fluorine-containing polyamide acid, the fluorine-containing polyamide and the fluorine-containing polyimide) according to the present invention are not particularly limited, as long as both components of the raw materials are dissolved therein. It is possible to use N,N-dimethylformamide (DMF), N,N-dimethylacetamide (DMAc), dimethylsulfoxide (DMSO), phenol, o-cresol, N-methyl-2-pyrolidone, sulfolane, m-cresol, p-cresol, 3-chlorophenol, 4-chlorophenol, γ-butyrolactone, γ-valerolactone, δ-valerolactone, γ-caprolactone, ε-caprolactone, α-methyl-γ-butyrolactone, ethylene carbonate, propylene carbonate, triethylene glycol, acetophenone, 1,3-dimethyl-2-imidazolidinone, and the like. It is possible to use other organic solvents without particular limitation, such as butyl acetate, ethyl acetate, ethylcellosolve, butylcellosolve, 2-methylcellosolve acetate, ethylcellosolve acetate, butylcellosolve acetate, ethyl acetate, butyl acetate, isobutyl acetate, dibutyl ether, diethylene glycol dimethyl ether, propylene glycol methyl acetate, tetrahydrofuran, dimethoxyethane, diethoxyethane, methyl isobutyl ketone, diisobutyl ketone, cyclohexanone, methyl ethyl ketone, acetone, butanol, ethanol, methanol, xylene, toluene, chlorobenzene, terpene, mineral spirit, petroleum naphtha-series solvents, and the like.

A precipitation method is taken as a post-treatment method after the polymerization reactions of the fluorine-containing polymers (the fluorine-containing polyamide acid, the fluorine-containing polyamide and the fluorine-containing polyimide) according to the present invention. They are not particularly limited, as long as they are solvents in which the unreacted raw material monomers are dissolved and in which the fluorine-containing polymers precipitate. It can be used butyl acetate, ethyl acetate, ethylcellosolve, butylcellosolve, 2-methylcellosolve acetate, ethylcellosolve acetate, butylcellosolve acetate, ethyl acetate, isobutyl acetate, dibutyl ether, diethylene glycol dimethyl ether, propylene glycol methyl acetate, tetrahydrofuran, dimethoxyethane, diethoxyethane, methyl isobutyl ketone, diisobutyl ketone, cyclohexanone, methyl ethyl ketone, acetone, butanol, ethanol, methanol, isopropyl alcohol, hexane, xylene, toluene, chlorobenzene, terpene, mineral spirit, petroleum naphtha-series solvents, and the like.

The fluorine-containing polymers (the fluorine-containing polyamide acid, the fluorine-containing polyamide and the fluorine-containing polyimide) in the present invention that are each soluble in dimethylacetamide (DMAc) are dissolved in the solvent at a concentration 0.1 g/dl, and reduced viscosity measured at 30° C. with an Ostwald viscosimeter is preferably 0.01 dl/g or greater, particularly preferably 0.3 dl/g or greater. Upon producing a film of the fluorine-containing polymer, one having a reduced viscosity of 0.01 dl/g or greater is preferable in order to maintain shape, and one having a reduced viscosity of 0.3 dl/g or greater is particularly preferable in order to secure strength.

It can be used the fluorine-containing polymer (the fluorine-containing polyamide acid, the fluorine-containing polyamide and the fluorine-containing polyimide) of the present invention under a varnish condition, where it is dissolved in an organic solvent, powder condition, film condition or solid condition. In case that it is used as a varnish, it can be applied on a base member of glass, silicon wafer, metal, metal oxide, ceramic, resin or the like by a generally used method such as spin coating, spray coating, flow coating, impregnation coating, brush coating or the like.

Speaking of electronic material use, it is effective to make materials have lower dielectric constants in order to reduce the signal delay within a semiconductor device, and it is effective to make materials have a uniform thermal expansion coefficient in order to prevent cracks at an interface between different materials (Since organic materials are greater than inorganic materials in expansion coefficient, having a uniform thermal expansion coefficient in organic materials corresponds to lowering thermal expansion). In particular, a hexafluoroisopropanol group-containing polyimide in the present invention is superior in terms of having both characteristics of lowering dielectric constant and lowering thermal expansion coefficient, and it has solubility in alkali aqueous solutions.

In the following, examples of the present invention are explained, but the present invention is not limited by these examples.

EXAMPLE 1

Figure 1:
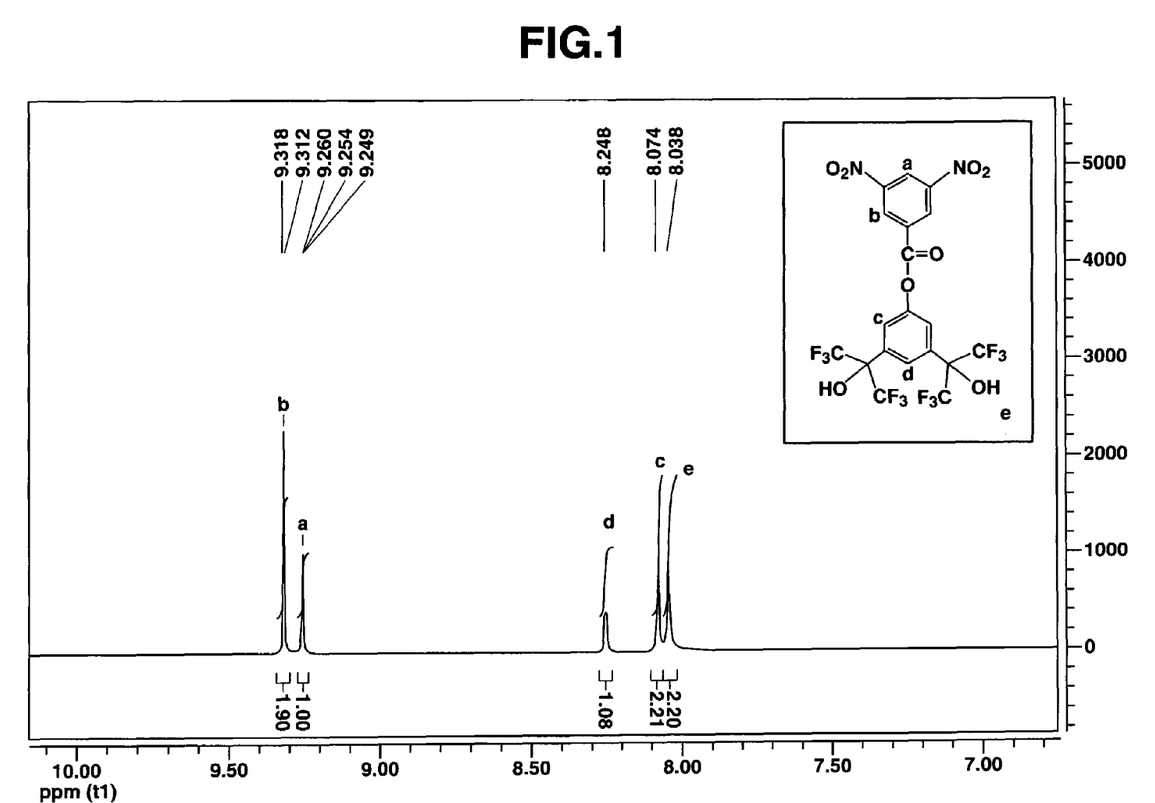
FIG. 1 shows $^1$H-NMR spectrum of a dinitro compound (formula (9)) obtained by Example 1.

20.00 g of the compound of the formula (8), 10.82 g of 3,5-dinitrobenzoylchloride, 4.6 ml of pyridine, and 150 ml of methylene chloride were added into a 300 ml three-necked flask. Stirring was conducted under nitrogen atmosphere at 40° C. for 3 hr. The reaction liquid was added into a 0.6N—HCl aqueous solution. The obtained white-color precipitate was recovered by filtration, followed by vacuum drying at room temperature. A white-color powder of 20.97 g (yield: 72%) was obtained. A structure of the formula (9) shown in the following was suggested by NMR spectrum. NMR spectrum is shown in FIG. 1.

[Chemical Formula 13]

(9)

EXAMPLE 2

Figure 2:
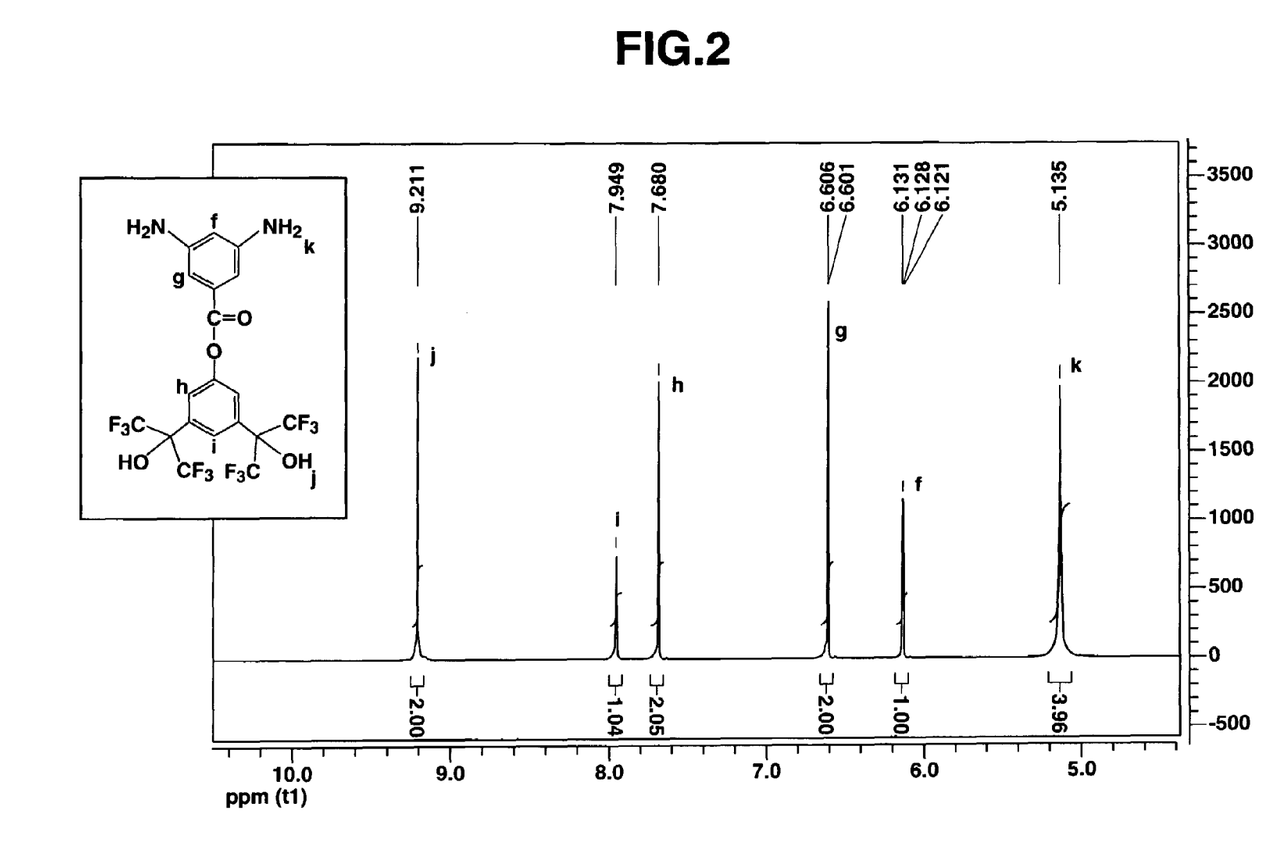
FIG. 2 shows $^1$H-NMR spectrum of a fluorine-containing diamine (formula (1)) obtained by Example 2.

9.90 g of the compound (the formula (9)) obtained by Example 1, 0.97 g of 10%-palladium carbon, and 75 ml of N,N-dimethylformamide (DMF) were added to a 300 ml three-necked flask. It was equipped with a hydrogen balloon, and stirring was conducted at room temperature for 12 hr. The reaction mixture was subjected to a Cellite treatment. The obtained filtrate was added to water, and the obtained precipitate was recovered. A recrystallization purification was conducted with a mixed solvent of methanol and water, thereby obtaining a white-color powder of 5.13 g (yield: 57%). The structure of the formula (1) was indicated by NMR spectrum. NMR spectrum is shown in FIG. 2.

EXAMPLE 3

Figure 3:
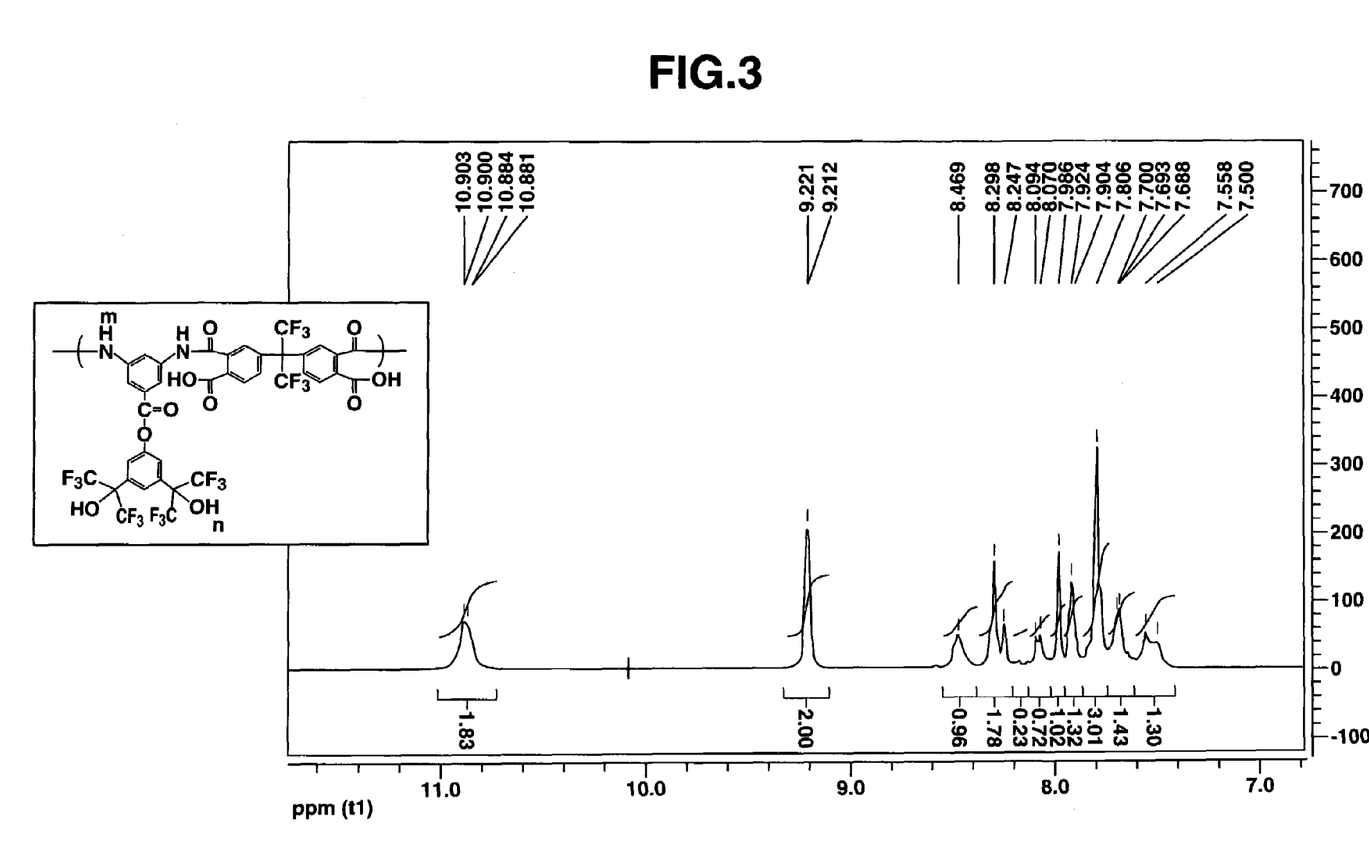
FIG. 3 shows $^1$H-NMR spectrum of a fluorine-containing polyamide acid (formula (10)) obtained by Example 3.

A 100 ml three-necked flask equipped with a stirring device was charged with 1.50 g of the fluorine-containing diamine (the formula (1)) obtained by Example 2, 1.19 g of 6FDA (2,2-bis(3,4-dicarboxyphenyl)hexafluoropropanoic dianhydride), and 10.8 ml of N,N-dimethylacetamide (DMAc). Stirring was conducted under nitrogen gas flow at room temperature for 5 hr. The reaction solution was added to a mixed solvent of methanol and water, thereby precipitating a polymer. The precipitated polymer was separated by filtration, followed by vacuum drying at 50° C., thereby obtaining 2.50 g (yield: 95%) of a fluorine-containing polyamide acid. It was dissolved in DMAc to have a concentration of 0.1 g/dl. Intrinsic viscosity measured at 30° C. with an Ostwald viscosimeter was 0.44 dl/g. Structure of the obtained polyamide acid was checked by IR and $^1$H-NMR spectrum, and thereby it was suggested to be the following formula (10). $^1$H-NMR spectrum is shown in FIG. 3.

[Chemical Formula 14]

(10)

EXAMPLE 4

The polymer (the formula (10)) obtained by Example 3 was dissolved in dimethylacetamide (DMAc), followed by spreading on a glass plate and then heating treatment at 250° C., thereby obtaining a tough film high in transparency. The structure was found from IR spectrum of the obtained film to be the following fluorine-containing polyimide (the formula (11)). The measurement of dielectric constant of the obtained fluorine-containing polyimide film was conducted, and it was 2.5 at 1 MHz. Linear thermal expansion coefficient of this film was measured, and its average value of 50-300° C. was $4 \times 10^{-5}$/° C. This film was soluble in 2.38 wt % tetramethylammonium aqueous solution.

EXAMPLE 5

Figure 4:
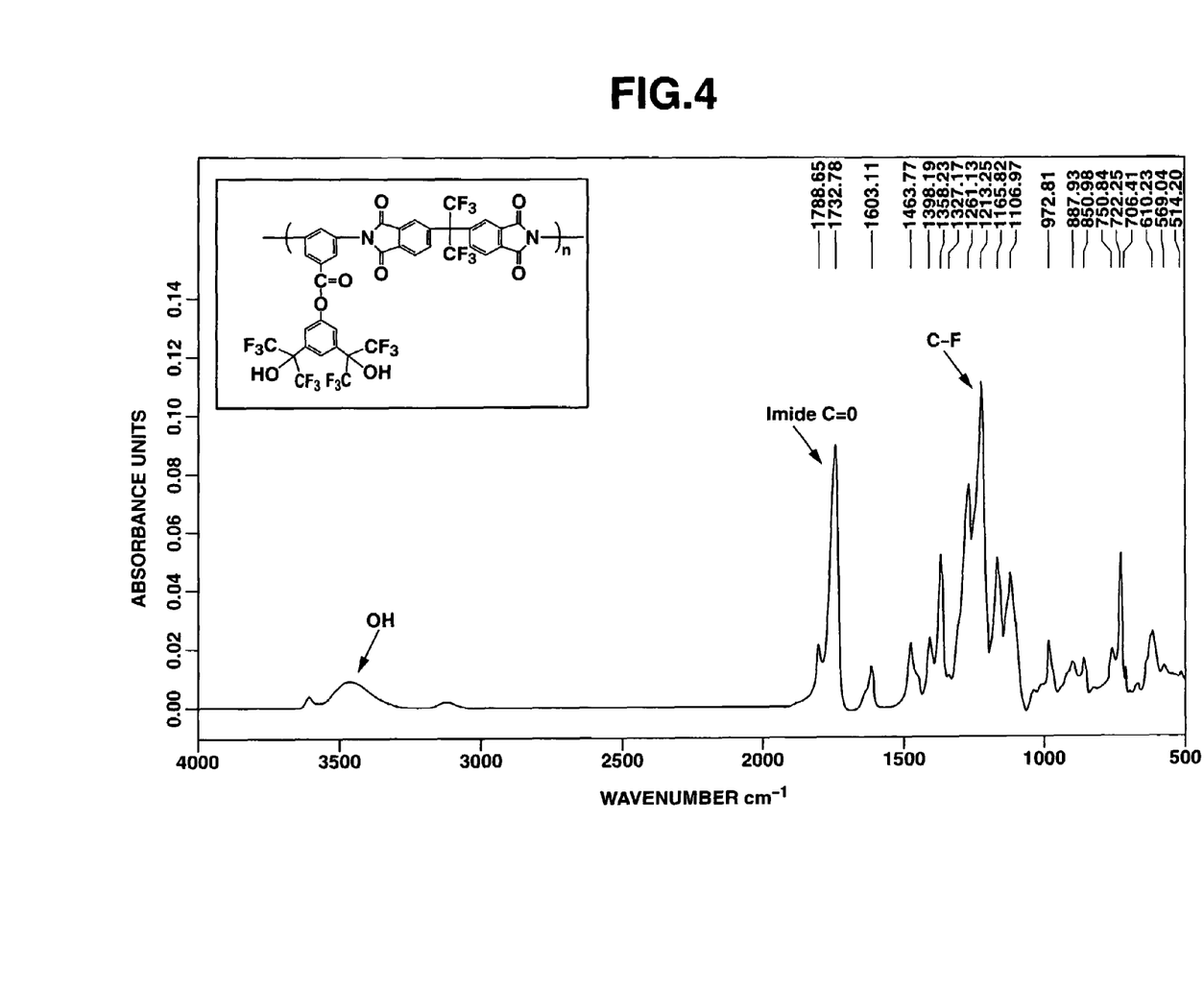
FIG. 4 shows infrared absorption spectrum of a fluorine-containing polyimide (formula (11)) obtained by Example 5.

0.50 g of the polyamide acid (the formula (10)) obtained by Example 3, 0.10 g of pyridine, 0.13 g of acetic anhydride, and 4.5 g of DMF were added to a 100 ml three-necked flask. Stirring was conducted under nitrogen atmosphere at 110° C. for 12 hr. The reaction solution was added to a mixed solvent of methanol and water, thereby precipitating a polymer. The precipitated polymer was separated by filtration, followed by vacuum drying at 100° C., thereby obtaining 0.43 g (yield: 90%) of the fluorine-containing polyimide. The obtained polyimide was found from a structural analysis by IR and $^1$H-NMR spectrum to have a chemical structure of the formula (11). It was dissolved in DMAc at a concentration of 0.1 g/dl, and intrinsic viscosity measured at 30° C. with an Ostwald viscosimeter was 0.30 dl/g. The obtained IR spectrum is shown in FIG. 4. The fluorine-containing polyimide (the formula (11)) obtained by the chemical imidization showed good solubility in low-boiling-point organic solvents, such as acetone, methanol, tetrahydrofuran, and propylene glycol monomethyl ether acetate, and 2.38% tetramethylammonium aqueous solution, as well as DMF and DMAc.

EXAMPLE 6

A 100 ml three-necked flask equipped with a stirring device was charged with 1.50 g of the diamine (the formula (1)) obtained by Example 2, 1.15 g of 2,2-bis(3-carboxyphenyl)hexafluoropropanoic dichloride, and 10.8 ml of N,N-dimethylacetamide (DMAc). Stirring was conducted under nitrogen gas flow at room temperature for 5 hr. The reaction solution was added to a mixed solvent of methanol and water, thereby precipitating a polymer. The precipitated polymer was separated by filtration, followed by vacuum drying at 100° C., thereby obtaining 2.38 g (yield: 95%) of a fluorine-containing polyamide (the formula (12)). It was dissolved in DMAc at a concentration of 0.1 g/dl, and intrinsic viscosity measured at 30° C. with an Ostwald viscosimeter was 0.40 dl/g. Structure of the obtained polyamide acid was checked by IR and $^1$H-NMR spectrum.

[Chemical Formula 15]

(11)

[Chemical Formula 16]

(12)

The invention claimed is:

1. A fluorine-containing diamine represented by the formula (1),

[Chemical Formula 17]

(1)

2. A fluorine-containing, polyamide acid that is a polymer obtained by reacting a diamine represented by the formula (1),

[Chemical Formula 18]

(1)

with a tetracarboxylic acid represented by the formula (2),

[Chemical Formula 19]

(2)

or tetracarboxylic dianhydride represented by the formula (3),

[Chemical Formula 20]

(3)

and that is represented by the formula (4),

[Chemical Formula 21]

(4)

wherein R is a tetravalent organic group containing an aromatic ring, and the carbonyl carbons are bonded to the aromatic ring in the ortho positions to each other to form imide five-membered rings.

3. A fluorine-containing polyimide resin that is a polymer obtained by dehydrating a fluorine-containing polyamide acid represented by the formula (4),

[Chemical Formula 22]

(4)

and that is represented by the formula (5),

[Chemical Formula 23]

wherein R is the same as in the formula (4)).

4. A fluorine-containing polyimide resin according to claim 3, wherein R is an organic group represented by the following formula,

[Chemical Formula 24]

wherein each aromatic ring has unbonded arms in ortho position to each other, and hydrogen atoms of the aromatic ring may be replaced with halogen atoms.

5. A fluorine-containing polyamide resin that is a polymer obtained by reacting a diamine represented by the formula (1),

[Chemical Formula 25]

with one selected from a dicarboxylic acid, a dicarboxylic dihalide and a dicarboxylic diester, which are represented by the formula (6),

[Chemical Formula 26]

wherein $R^1$ is a bivalent organic group containing an aromatic ring, X is —OH group, halogen (fluorine, chlorine, bromine or iodine) atom or —OR' group, and R' represents an alkyl group or phenyl group, and that contains a constituent unit represented by the formula (7),

[Chemical Formula 27]

wherein $R^1$ is the same as in formula (6).

6. A fluorine-containing polyamide resin according to claim 5, wherein $R^1$ is an organic group represented by the following formula,

[Chemical Formula 28]

wherein hydrogen atoms of the aromatic ring may be replaced with halogen atoms.

* * * * *